United States Patent
Miller

(10) Patent No.: US 9,097,677 B1
(45) Date of Patent: Aug. 4, 2015

(54) MAGNETIC GAS SENSORS

(71) Applicant: Casey William Miller, Tampa, FL (US)

(72) Inventor: Casey William Miller, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/309,500

(22) Filed: Jun. 19, 2014

(51) Int. Cl.
*G01N 27/74* (2006.01)
*G01N 33/00* (2006.01)

(52) U.S. Cl.
CPC .............. *G01N 27/74* (2013.01); *G01N 33/005* (2013.01)

(58) Field of Classification Search
CPC .............................. G01N 27/74; G01N 27/76
USPC ........................................................ 73/31.05
See application file for complete search history.

(56) References Cited

U.S. PATENT DOCUMENTS

| | | | | |
|---|---|---|---|---|
| 4,949,039 | A | | 8/1990 | Grunberg |
| 5,821,129 | A | * | 10/1998 | Grimes et al. ................ 436/151 |
| 6,393,921 | B1 | * | 5/2002 | Grimes et al. .................. 73/728 |
| 7,836,752 | B2 | | 11/2010 | Punnoose |
| 7,916,306 | B2 | * | 3/2011 | Iannuzzi et al. ............... 356/501 |
| 8,826,726 | B2 | * | 9/2014 | Schmid et al. ............... 73/31.05 |
| 2006/0055392 | A1 | | 3/2006 | Passmore |
| 2006/0060776 | A1 | | 3/2006 | Punnoose |
| 2008/0151615 | A1 | | 6/2008 | Rodmacq |
| 2009/0002714 | A1 | * | 1/2009 | Iannuzzi et al. ............... 356/477 |
| 2012/0131988 | A1 | * | 5/2012 | Schmid et al. ............... 73/25.02 |

FOREIGN PATENT DOCUMENTS

| | | |
|---|---|---|
| DE | 3820475 C1 | 12/1989 |
| EP | 0958502 B1 | 11/1999 |
| EP | 2426483 A1 | 7/2012 |
| WO | WO2006080558 A1 | 11/2006 |

OTHER PUBLICATIONS

Punnoose, et al. "Novel Magnetic Hydrogen Sensing: A Case Study Using Antiferromgnetic Haematite Nanoparticles", IOP Publishing Ltd., Mar. 23, 2007.

* cited by examiner

*Primary Examiner* — Peter Macchiarolo
*Assistant Examiner* — Nathaniel Kolb
(74) *Attorney, Agent, or Firm* — Thomas | Horstemeyer, LLP

(57) ABSTRACT

In one embodiment, a magnetic gas sensor includes a first ferromagnetic layer, a second ferromagnetic layer, and a gas-sensitive metallic interlayer positioned between the first and second ferromagnetic layers, wherein at least one physical property of the metallic interlayer changes in the presence of a gas that is to be detected, wherein a magnetic coupling between the first and second ferromagnetic layers, and a magnetic state of the sensor, can change depending upon the state of the physical property of the metallic interlayer.

15 Claims, 5 Drawing Sheets

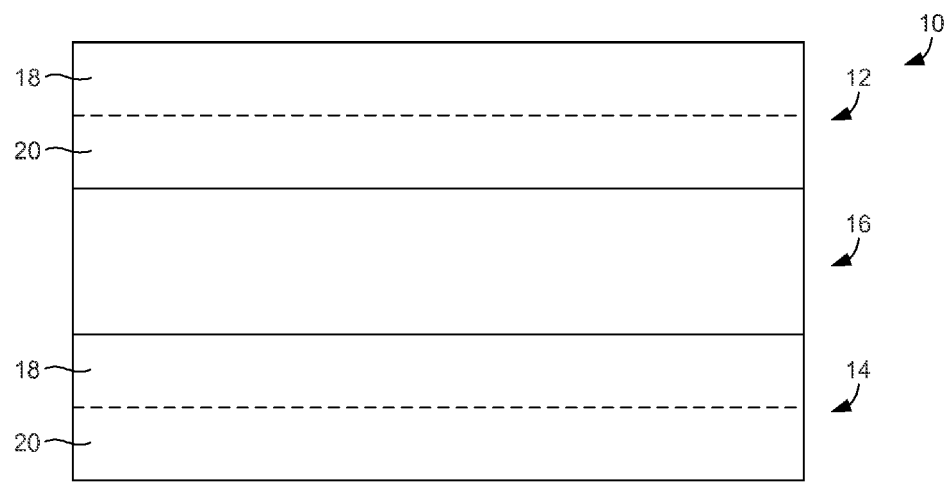
FIG. 1
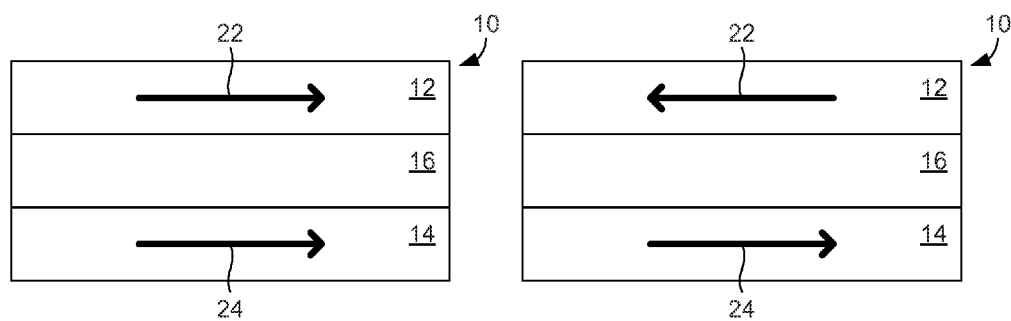
FIG. 2A  FIG. 2B

MAGNETIC GAS SENSORS

BACKGROUND

Hydrogen gas sensors are used in various applications, including battery rooms, battery cabinet systems, battery charging areas, and hydrogen fueled back-up power systems. While conventional hydrogen gas sensor designs are viable, it would be desirable to have alternative designs that enable alternative functionality, such as remote sensing.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 1 is a side view of a first embodiment of a magnetic gas sensor.

FIGS. 2A and 2B are side views that illustrate two different magnetic states for the sensor of FIG. 1.

DETAILED DESCRIPTION

Figure 3:
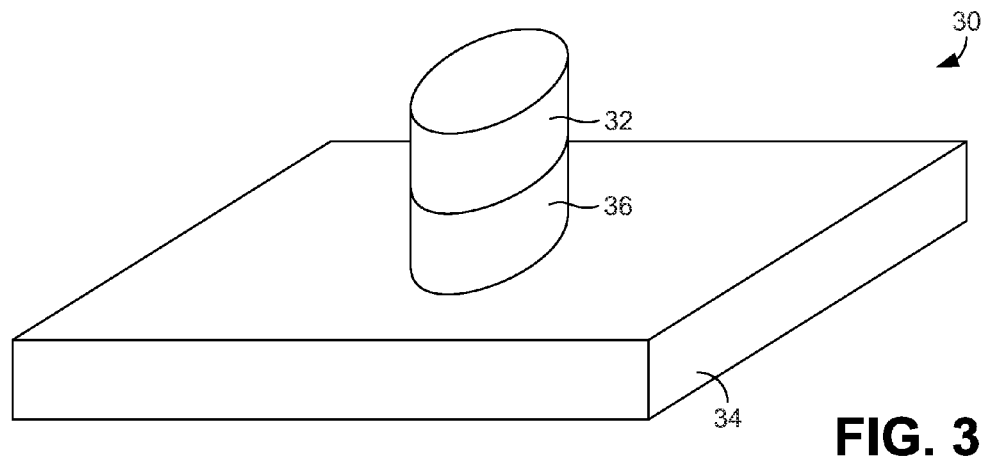
FIG. 3 is a perspective view of a second embodiment of a magnetic gas sensor.

As described above, it would be desirable to have alternative gas sensor designs. Disclosed herein are magnetic gas sensors that can be used to detect the presence of a gas, such as hydrogen gas. In some embodiments, the sensors comprise a thin gas-sensitive metallic layer that is positioned between two ferromagnetic layers. The sensors can have a first magnetic state when no hydrogen gas is present, and a second magnetic state in the presence of hydrogen gas. The change in magnetic state can be detected optically, electrically, or magnetoelectrically.

In the following disclosure, various specific embodiments are described. It is to be understood that those embodiments are example implementations of the disclosed inventions and that alternative embodiments are possible. All such embodiments are intended to fall within the scope of this disclosure.

FIG. 1 illustrates an embodiment of a magnetic gas sensor 10. It will be assumed for purposes of this discussion that the sensor 10 is a hydrogen gas sensor. As indicated in FIG. 1, the sensor 10 comprises multiple layers including a first (top) ferromagnetic layer 12, a second (bottom) ferromagnetic layer 14, and a gas-sensitive (e.g., hydrogen gas-sensitive) metallic interlayer 16 that is positioned between the ferromagnetic layers.

Each ferromagnetic layer 12, 14 is made of a ferromagnetic material. Examples include iron, cobalt, nickel, gadolinium, or an alloy including one or more of those materials (e.g., NiFe, FeCo, CoFeB, FeV). In some embodiments, one or both of the ferromagnetic layers 12, 14 can be a single layer of material. In other embodiments, one or both of the ferromagnetic layers 12, 14 can be a heterostructure that includes multiple layers of material. For example, as indicated in FIG. 1, the ferromagnetic layers 12, 14 can comprise first and second sub-layers 18, 20 that together form the ferromagnetic layers. By way of example, the sub-layers 18, 20 can comprise cobalt and palladium, cobalt and nickel, cobalt and palladium, a cobalt-iron-boron alloy (CoFeB) and a magnesium-oxide alloy (MgO), a nickel-iron alloy (NiFe) and gadolinium, etc. It is also noted that one sub-layer can be a ferromagnetic layer and the other sub-layer can be an antiferromagnetic layer. In some embodiments, the antiferromagnetic layer can be made of an iridium-manganese alloy (IrMn), an iron-manganese alloy (FeMn), or a platinum-manganese alloy (PlMn). While only two sub-layers 18, 20 have been shown in FIG. 1, it is noted that one or both ferromagnetic layers 12, 14 can comprise more than two sub-layers. Regardless of whether or not the ferromagnetic layers 12, 14 comprise a single layer or multiple layers of material, each ferromagnetic layer can be approximately 0.3 to 50 nm thick.

Each ferromagnetic layer 12, 14 has an inherent magnetization orientation. In some embodiments, one or both of the ferromagnetic layers 12, 14 has an in-plane magnetic anisotropy in which case the direction of the magnetization vector is parallel to the layer. Such an arrangement is illustrated in FIGS. 2A and 2B, which are described below. In other embodiments, one or both of the ferromagnetic layers 12, 14 has a perpendicular magnetic anisotropy, in which case the direction of the magnetization vector is perpendicular to the layer.

The metallic interlayer 16 is made of a material wherein one or more of the physical properties of the material changes in the presence of hydrogen gas. Examples include palladium, yttrium, magnesium-based alloys, lanthanides, or an alloy of one or more of those materials. The property that changes in the presence of hydrogen gas depends upon the material that is used. For example, when palladium is used, hydrogen gas molecules enter the material lattice of the palladium and cause it to expand. On the other hand, the resistivity of yttrium, magnesium-based alloys, and lanthanides changes in the presence of hydrogen gas. In some cases, the presence of hydrogen gas will even cause a metal-to-insulator transition. As described below, these property changes affect the magnetic coupling between the ferromagnetic layers 12, 14, and therefore the magnetic state of the sensor 10. In particular, expansion and decreased resistivity reduces the strength of this magnetic coupling. Regardless of the material that is used to construct the metallic interlayer 16, it can also be approximately 1 to 10 nm thick.

FIGS. 2A and 2B illustrate two example magnetization states for the sensor 10. In both figures, the ferromagnetic layers 12, 14 exhibit in-plane magnetic anisotropy, in which case their magnetization vectors 22, 24 are both parallel to the layers. In FIG. 2A, the sensor 10 is in a parallel state in which the vectors 22, 24 face the same direction. In FIG. 2B, the sensor 10 is in an antiparallel state in which the vectors 22, 24 face opposite directions. The different states shown in FIGS. 2A and 2B can be the result of the thickness of the metallic interlayer 16. In particular, the thickness of the metallic interlayer can control the relative coupling between the two ferromagnetic layers 12, 14. For different thicknesses, the strength of the coupling, and even its sign, can change. The strength of the coupling can be expressed by the coupling constant, J. If J is greater than zero, the parallel state shown in FIG. 2A results. If, on the other hand, J is less than zero, the antiparallel state shown in FIG. 2B results.

The different states shown in FIGS. 2A and 2B can alternatively be the result of exposure of the sensor 10 to hydrogen gas. For example, the magnetic orientation shown in FIG. 2A can be the orientation of the sensor 10 when no hydrogen gas is present and the magnetic orientation shown in FIG. 2B can be the orientation when hydrogen gas is present. As indicated above, this change can be effected by a change in a property of the metallic layer 16 that alters the magnetic coupling between the ferromagnetic layers 12, 14. It is noted that the sensor 10 can, alternatively, exhibit the magnetic orientation shown in FIG. 2A when hydrogen gas is present and the magnetic orientation shown in FIG. 2B when hydrogen gas is not present. The orientations depend upon the configuration of the sensor. In addition, a constant external magnetic field can be applied to alter its magnetic orientation, if desired.

The sensor can be designed so as to control the magnetization direction of the first ferromagnetic layer when it changes due to the presence of hydrogen gas to more predictably detect that presence. In some embodiments, shape anisotropy can be utilized to define the orientation of the magnetization. Such an embodiment is illustrated in FIG. 3. As shown in this figure, a magnetic gas sensor 30 comprises a first (top) ferromagnetic layer 32, a second (bottom) ferromagnetic layer 34, and a gas-sensitive metallic interlayer 36 that is positioned between the ferromagnetic layers, each of which can be composed of a material such as those described above for the like-named components shown in FIG. 1.

As is apparent in FIG. 3, the first ferromagnetic layer 32 and the metallic interlayer 36 together form a member that extends upward from the second ferromagnetic layer 34 having an elliptical cross-section so that they are elongated and have a long (major) axis and a short (minor) axis. Although the second ferromagnetic layer 34 is shown as having a larger rectangular shape, it is noted that it can have a shape similar to that of the first ferromagnetic layer 32 and the metallic interlayer 36. Because of the elliptical shape and the phenomenon of shape anisotropy, the first ferromagnetic layer 32 inherently has a magnetization orientation that extends along the direction of the major axis of the ellipse. In the configuration shown in FIG. 3, the shape anisotropy, K, of the elliptical shape competes with the magnetic coupling, J, between the first and second ferromagnetic layers 32, 34. When J is much greater than K, the magnetizations of the first and second ferromagnetic layers 32, 34 will be collinear. When K is much greater than J, however, the magnetizations of the first and second ferromagnetic layers 32, 34 will be non-collinear.

Figure 4A:
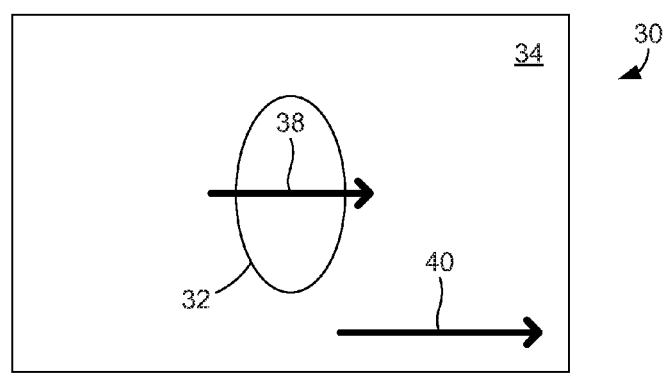
FIGS. 4A and 4B are side views that illustrate two different magnetic states for the sensor of FIG. 3.
Figure 4B:
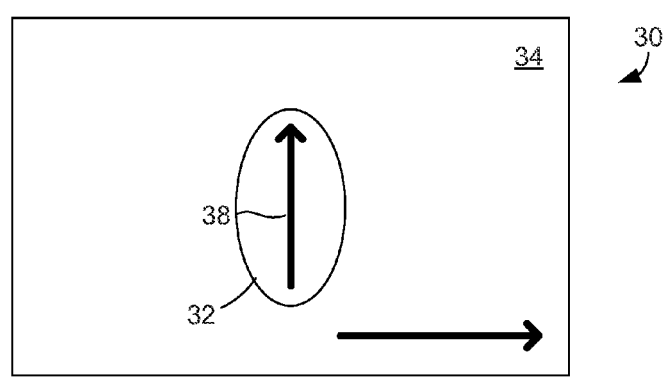

This above-described phenomenon can be exploited in the gas sensing context, of which FIGS. 4A and 4B provide an example. FIGS. 4A and 4B respectively show example magnetization vectors 38, 40 for the first and second ferromagnetic layers 32, 34 of the sensor 30. In FIG. 4A, the sensor 30 is not exposed to hydrogen gas. In FIG. 4B, however, the sensor 30 is exposed to hydrogen gas. As is apparent in FIG. 4A, when the sensor is not exposed to hydrogen gas, the magnetic coupling between the ferromagnetic layers 32, 34 is much greater than the shape anisotropy of the elliptical shape. Accordingly, the magnetizations vectors 38 and 40 are collinear. In FIG. 4B, however, a property change in the metallic interlayer 36 (e.g., either expansion of the layer or reduction in conductivity of the layer) has altered the sensor 30 such that the magnetic coupling is sharply decreased, in which case the shape anisotropy is much greater than the magnetic coupling. As a result, the magnetization vector 38 has changed direction so that it extends along the direction of the major axis of the ellipse so as to be non-collinear with the magnetization vector 40. As described below, this change in the sensor's magnetic state can be detected so that the presence of the hydrogen gas can be detected. It is noted that while the angles made between the magnetization vectors 38, 40 can be parallel and orthogonal as shown in FIGS. 4A and 4B, the angle they form can be vary as a function of gas concentration.

Figure 5A:
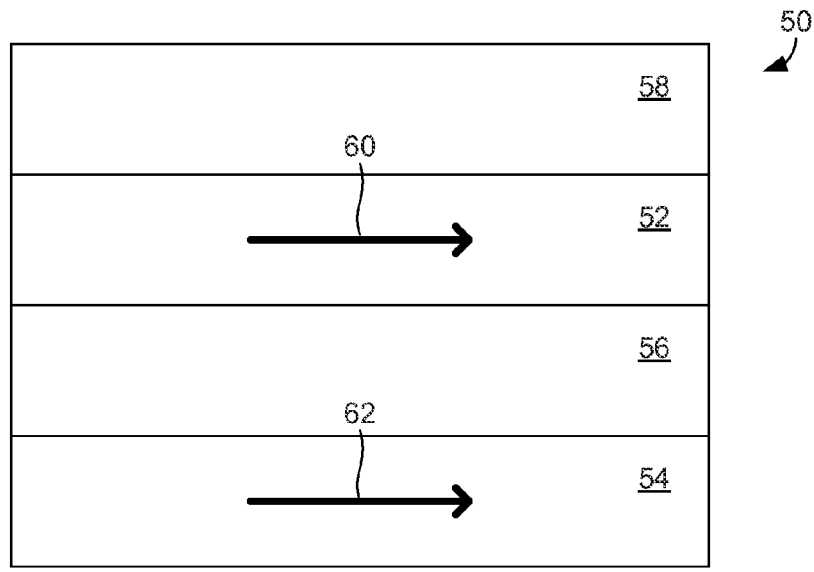
FIGS. 5A and 5B are side views of a third embodiment of a magnetic gas sensor, showing two different magnetic states for the sensor.
Figure 5B:
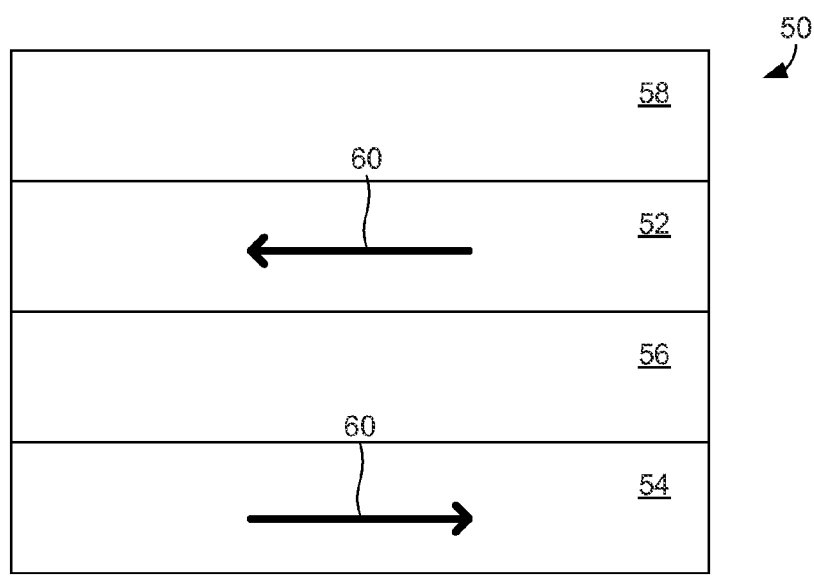

In other embodiments, the magnetization direction of the first ferromagnetic layer can be controlled by using a further magnetic element, such as a natural or synthetic antiferromagnetic. FIGS. 5A and 5B illustrate an example of this. As shown in these figures, a magnetic gas sensor 50 comprises a first (top) ferromagnetic layer 52, a second (bottom) ferromagnetic layer 54, and a gas-sensitive metallic interlayer 56 that is positioned between the ferromagnetic layers, each of which can be composed of a material such as those described above for the like-named components shown in FIG. 1. In addition, however, the sensor 50 includes an antiferromagnetic layer 58 that is formed on top of the first ferromagnetic layer 52. In some embodiments, the antiferromagnetic layer 58 is made of a manganese-based alloy, such as iridium manganese, iron manganese, or platinum manganese.

In the embodiment of FIGS. 5A and 5B, there is magnetic coupling between the first ferromagnetic layer 52 and the second ferromagnetic layer 54 as before, but also magnetic coupling between the first ferromagnetic layer and the antiferromagnetic layer 58. These two magnetic couplings complete with each other for control of the magnetic orientation of the first ferromagnetic layer 52 and therefore define the overall magnetic state of the sensor 50.

When the properties of the metallic interlayer 56 change because of the presence of hydrogen gas, the magnetic coupling between the first and second ferromagnetic layers 52, 54 is altered (e.g., weakened), which can affect the magnetization orientation of the first ferromagnetic layer 52. This is illustrated in the figures. It is assumed that the sensor 50 is not exposed to hydrogen gas in FIG. 5A but is exposed to hydrogen gas in FIG. 5B. In FIG. 5A, the magnetic coupling between the first and second ferromagnetic layers 52, 54 is much stronger than the magnetic coupling between the first ferromagnetic layer and the antiferromagnetic layer 58. As a result, the magnetization vector 60 of the first ferromagnetic layer 52 is parallel to the magnetization vector 62 of the second ferromagnetic layer 54. In FIG. 5B, however, the magnetic coupling between the first and second ferromagnetic layers 52, 54 is much weaker than the magnetic coupling between the first ferromagnetic layer and the antiferromagnetic layer 58 because of the property change within the metallic interlayer 56. Assuming that the magnetization couplings are opposite in sign, the magnetization vector 60 of the first ferromagnetic layer 52 will then be antiparallel to the magnetization vector 62 of the second ferromagnetic layer 54.

While the antiferromagnetic layer 58 has been shown as being formed on top of the first ferromagnetic layer 52 in FIGS. 5A and 5B, it is noted that the antiferromagnetic layer 58 could alternatively be formed on the second ferromagnetic layer 54. In other embodiments, antiferromagnetic layers could be formed on both ferromagnetic layers 52, 54. It is also noted that the sensor 50 can be in an antiparallel state in the absence of hydrogen gas and in the parallel state in the presence of hydrogen gas.

Figure 6A:
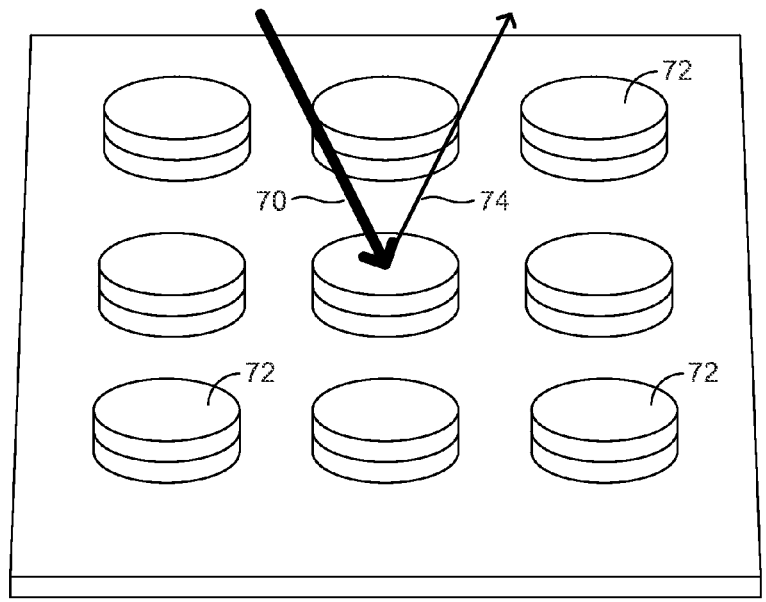
FIGS. 6A and 6B are perspective views illustrating an embodiment of optical detection of a magnetic state of a magnetic gas sensor.
Figure 6B:
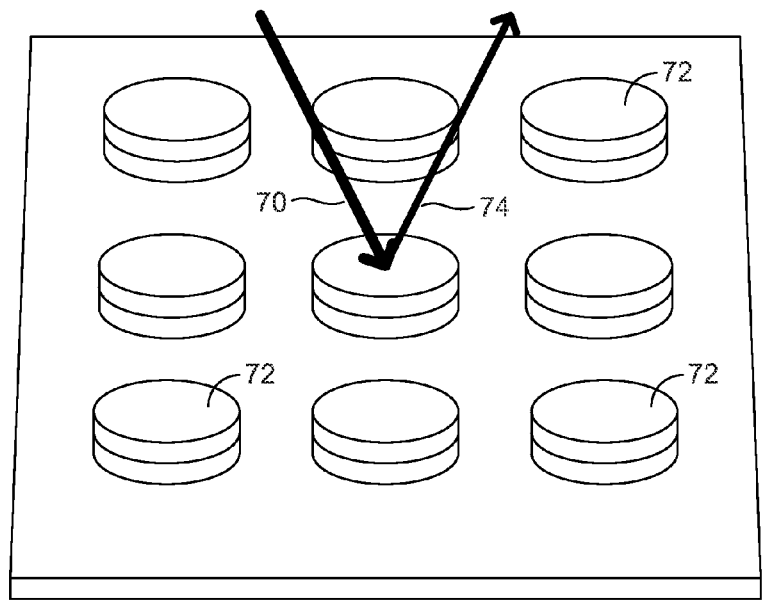

Regardless of the manner in which a magnetization state change is effected or controlled, the change in state can be detected optically, electrically, or magnetoelectrically. FIGS. 6A and 6B illustrate an example of optical detection. In these figures, a beam of light 70 from a light source, such as a laser beam emitted from a laser, is focused on one or more elliptical magnetic gas sensors 72 having a construction similar to that described above in relation to FIG. 3. It is noted that a similar detection scheme could be used for embodiments that include an antiferromagnetic layer, as in FIGS. 5A and 5B. The light that impinges upon the sensor(s) 72 is reflected and can be detected by a suitable light detector. The intensity of the reflected light 74 can then be used to determine whether or not hydrogen gas is present.

In this example, it is assumed that hydrogen gas is not present in FIG. 6A but is present in FIG. 6B. In the no-hydrogen-present case (FIG. 6A), the sensors 72 have anti-parallel magnetization. As a result, the intensity of the reflected light 74 is relatively small (as indicated with a narrow arrow). In the hydrogen-present case (FIG. 6B), the sensors 72 have parallel magnetization. As a result, the intensity of the reflected light 74 is relatively large (as indicated with a thicker arrow). Although the intensity of the reflected light has been described, it is noted that the direction of polarization of the light can alternatively be used to detect a change in the magnetization states of the sensors 72.

Figure 7A:
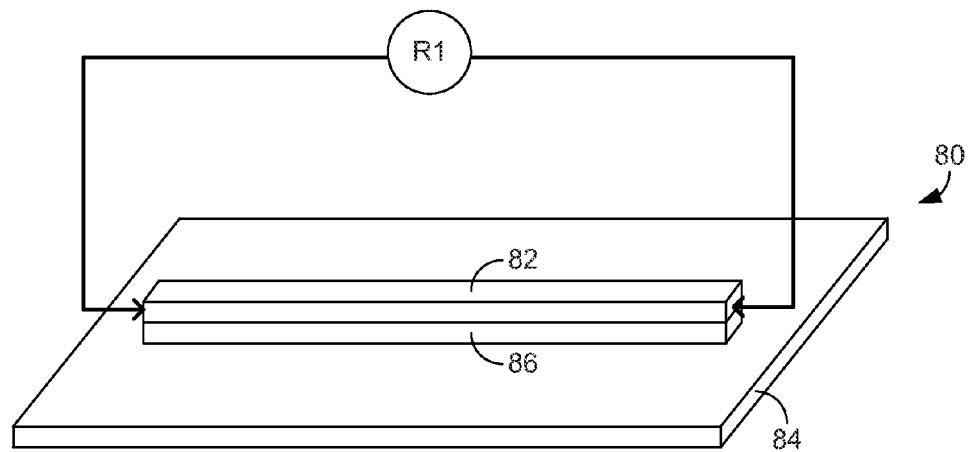
FIGS. 7A and 7B are perspective views illustrating an embodiment of electrical or magnetoelectrical detection of a magnetic state of a magnetic gas sensor.
Figure 7B:
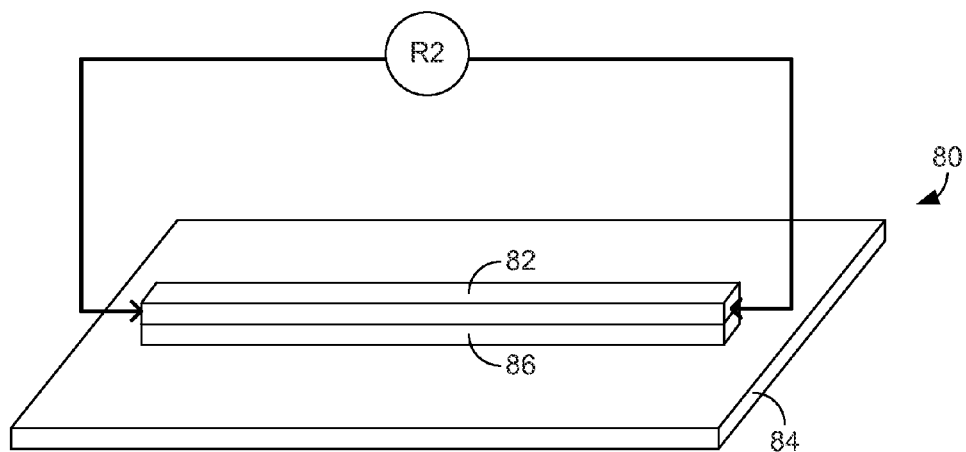

FIGS. 7A and 7B illustrate electrical and magnetoelectrical detection. In this embodiment, a magnetic gas sensor 80 comprises a first (top) ferromagnetic layer 82, a second (bottom) ferromagnetic layer 84, and a gas-sensitive metallic interlayer 86 that is positioned between the ferromagnetic layers. The first ferromagnetic layer 82 and the metallic interlayer 86 together form an elongated beam that extends along the surface of the second ferromagnetic layer 84. As indicated in the figures, the resistance of the sensor 80, which changes in the presence of hydrogen, can be measured by applying a voltage to the beam. When magnetoelectrical detection is performed, the resistance can be measured while applying a magnetic field to the sensor 80. In the example of FIGS. 7A and 7B, it is assumed that hydrogen gas is not present in FIG. 7A but is present in FIG. 7B. As can be appreciated from FIGS. 7A and 7B, different resistances are measured in the two different cases. Although not illustrated, the sensor 80 can include an antiferromagnetic layer, as in the embodiment of FIGS. 5A and 5B.

The invention claimed is:

1. A magnetic gas sensor comprising:
   an elongated first ferromagnetic layer having a long axis, a short axis, and a shape anisotropy that results in a magnetization direction aligned with the long axis;
   a second ferromagnetic layer; and
   a gas-sensitive metallic interlayer positioned between the first and second ferromagnetic layers, wherein at least one physical property of the metallic interlayer changes in the presence of a gas that is to be detected;
   wherein a magnetic exchange coupling between the first and second ferromagnetic layers, and a magnetic state of the sensor, can change depending upon the state of the physical property of the metallic interlayer and wherein the shape anisotropy of the first ferromagnetic layer competes with the magnetic exchange coupling between the first and second ferromagnetic layers.

2. The magnetic gas sensor of claim 1, wherein at least one of the ferromagnetic layers comprises a single layer of material.

3. The magnetic gas sensor of claim 2, wherein at least one of the ferromagnetic layers comprises iron, cobalt, nickel, gadolinium, or an alloy including one or more of those materials.

4. The magnetic gas sensor of claim 1, wherein at least one of the ferromagnetic layers comprises a heterostructure comprising multiple sub-layers.

5. The magnetic gas sensor of claim 4, wherein at least one of the ferromagnetic layers comprises a sub-layer comprising cobalt, palladium, nickel, iron, boron, magnesium, gadolinium, or an alloy including one or more of those materials.

6. The magnetic gas sensor of claim 1, wherein each layer is approximately 0.3 to 50 nanometers thick.

7. The magnetic gas sensor of claim 1, wherein the gas-sensitive metallic interlayer comprises palladium, yttrium, magnesium-based alloys, lanthanides, or an alloy of one or more of those materials.

8. The magnetic gas sensor of claim 1, wherein the gas-sensitive metallic interlayer expands in the presence of the gas to be detected and this expansion reduces the magnetic exchange coupling between the ferromagnetic layers.

9. The magnetic gas sensor of claim 1, wherein a resistivity of the gas-sensitive metallic interlayer decreases in the presence of the gas to be detected and this decrease reduces the magnetic exchange coupling between the ferromagnetic layers.

10. The magnetic gas sensor of claim 1, wherein the gas-sensitive metallic interlayer is sensitive to hydrogen gas such that at least one physical property of the metallic interlayer changes in the presence of hydrogen gas.

11. The magnetic gas sensor of claim 1, wherein the first ferromagnetic layer is elliptical.

12. A magnetic hydrogen gas sensor comprising:
    an elliptical first ferromagnetic layer having a long axis, a short axis, and a shape anisotropy that results in a magnetization direction aligned with the long axis;
    a second ferromagnetic layer; and
    a hydrogen gas-sensitive metallic interlayer positioned between the first and second ferromagnetic layers, the metallic interlayer comprising palladium, yttrium, magnesium-based alloys, lanthanides, or an alloy of one or more of those materials, wherein at least one physical property of the metallic interlayer changes in the presence of hydrogen gas;
    wherein a magnetic exchange coupling between the first and second ferromagnetic layers, and a magnetic state of the sensor, can change depending upon the state of the physical property of the metallic interlayer and wherein the shape anisotropy of the first ferromagnetic layer competes with the magnetic exchange coupling between the first and second ferromagnetic layers.

13. A method of detecting a gas, the method comprising:
    forming a magnetic gas sensor comprising a first ferromagnetic layer, a second ferromagnetic layer, and a gas-sensitive metallic interlayer positioned between the first and second ferromagnetic layers, wherein at least one physical property of the metallic interlayer changes in the presence of a gas that is to be detected and the change of the physical property results in a change in a magnetic exchange coupling between the ferromagnetic layers;
    positioning the magnetic gas sensor in an environment in which a gas to be detected may be or become present;
    detecting a magnetic state of the sensor by focusing a beam of light on the sensor and detecting the intensity of light reflected from the sensor.

14. A magnetic gas sensor comprising:
    a first ferromagnetic layer;
    a second ferromagnetic layer;
    a gas-sensitive metallic interlayer positioned between the first and second ferromagnetic layers, wherein at least one physical property of the metallic interlayer changes in the presence of a gas that is to be detected; and
    an antiferromagnetic layer formed on top of the first ferromagnetic layer;
    wherein a magnetic exchange coupling between the first and second ferromagnetic layers, and a magnetic state of the sensor, can change depending upon the state of the physical property of the metallic interlayer and wherein the antiferromagnetic layer magnetically couples with the first ferromagnetic layer and that magnetic coupling competes with the magnetic exchange coupling between the first and second ferromagnetic layers.

15. A magnetic hydrogen gas sensor comprising:
a first ferromagnetic layer;
a second ferromagnetic layer;
a hydrogen gas-sensitive metallic interlayer positioned between the first and second ferromagnetic layers, the metallic interlayer comprising palladium, yttrium, magnesium-based alloys, lanthanides, or an alloy of one or more of those materials, wherein at least one physical property of the metallic interlayer changes in the presence of hydrogen gas; and
an antiferromagnetic layer formed on top of the first ferromagnetic layer
wherein a magnetic exchange coupling between the first and second ferromagnetic layers, and a magnetic state of the sensor, can change depending upon the state of the physical property of the metallic interlayer and wherein the antiferromagnetic layer magnetically couples with the first ferromagnetic layer and that magnetic coupling competes with the magnetic exchange coupling between the first and second ferromagnetic layers.

\* \* \* \* \*